United States Patent [19]

Siegel et al.

[11] Patent Number: 4,713,350

[45] Date of Patent: Dec. 15, 1987

[54] HYDROPHILIC ASSAY REAGENT CONTAINING ONE MEMBER OF SPECIFIC BINDING PAIR

[75] Inventors: Richard C. Siegel, Yorktown Heights; Christina S. Marx, Peekskill; Bartholomew Hargitay, White Pains; Neil Wotherspoon, New York, all of N.Y.

[73] Assignee: Technicon Instruments Corporation, Tarrytown, N.Y.

[21] Appl. No.: 544,749

[22] Filed: Oct. 24, 1983

[51] Int. Cl.$^4$ .............. G01N 33/546; G01N 33/545; G01N 33/543; G01N 33/549

[52] U.S. Cl. .................. 436/533; 436/518; 436/531; 436/532; 436/534; 436/808; 427/2

[58] Field of Search ............. 436/531, 532, 533, 534, 436/518, 548, 808; 435/180, 181; 427/2

[56] References Cited

U.S. PATENT DOCUMENTS

| | | | |
|---|---|---|---|
| 4,004,979 | 1/1977 | Avrameas | 435/181 X |
| 4,108,976 | 8/1978 | Reese | 436/808 X |
| 4,115,540 | 9/1978 | Digenis | 436/531 X |
| 4,210,418 | 7/1980 | Brown | 436/532 |
| 4,220,722 | 9/1980 | Rowley | 436/537 |
| 4,415,700 | 11/1983 | Batz | 436/533 X |
| 4,440,903 | 4/1984 | Golstein | 435/181 X |
| 4,547,466 | 10/1985 | Turanchik et al. | 436/533 X |
| 4,572,901 | 2/1986 | Ceriani et al. | 436/531 X |

FOREIGN PATENT DOCUMENTS

| | | | |
|---|---|---|---|
| 0141977 | 6/1980 | Fed. Rep. of Germany | 435/180 |
| 0051237 | 5/1981 | Japan | 435/182 |

*Primary Examiner*—Esther M. Kepplinger
*Assistant Examiner*—Jeremy M. Jay
*Attorney, Agent, or Firm*—Jeffrey M. Greenman

[57] ABSTRACT

This invention provides a hydrophilic specific binding assay reagent which is prepared by a process comprising the steps of reacting a partner of a specific binding pair and at least one hydrophilic substance with haloalkyl moieties associated with the surface of a solid phase and recovering the reagent so prepared from any unreacted binding partner. Preferably, the alpha-haloalkyl is chloromethyl and the at least one hydrophilic substance comprises at least one protein, such as albumin, and at least one non-proteinaceous amine to which the solid phase is impermeable, such as tris (hydroxymethyl) aminomethane. The specific binding assay reagent of the invention can be combined with other reagents to provide an assay composition.

20 Claims, No Drawings

HYDROPHILIC ASSAY REAGENT CONTAINING ONE MEMBER OF SPECIFIC BINDING PAIR

BACKGROUND OF THE INVENTION (1) Field of the Invention

This invention relates to the field of specific binding assays and reagents therefor, particularly those in which some of the reagents are bound to a solid phase and used to determine ligands in liquid samples containing interfering substances.

(2) Brief Description of the Prior Art

The development of specific binding assay techniques has provided extremely useful analytical methods for determining various organic substances of diagnostic, medical, environmental and industrial importance which appear in liquid media at very low concentrations. Specific binding assays are based on the specific interaction between a ligand, i.e., a bindable analyte under determination, and a binding partner therefor, i.e., receptor. Where one of the ligand and its binding partner is an antibody and the other is a corresponding hapten or antigen, the assay is known as an immunoassay.

These specific binding assays have been provided in a variety of solid state formats including analytical elements or test strips, coated tubes, particle-associated reagents and others. Agglutination assays are among the most widely used solid state specific binding assays, usually as immunoassays. They may be classified as direct, indirect (passive) or inhibition type agglutination assays. In a direct agglutination assay, particles having surface components which are one member of a specific binding pair (e.g., a receptor), are reacted with a sample to be assayed for the other member of the specific binding pair (e.g., ligand). In the indirect (passive) agglutination format, one member of a specific binding pair (e.g., receptor) is bound to a solid substrate particle, and this particle-bound member is reacted with a sample to be assayed for the other member of the pair (e.g., ligand). In inhibition-type agglutination assays, a sample to be tested for one binding pair member is reacted with a solution containing the other member of the binding pair and particles which contain (direct) or are bound with (indirect) the binding pair member suspected of being in the sample. Agglutination assays have been summarized in the literature. See, for example, Bellanti, *Immunology*, W. B. Saunders Co., Philadelphia (1971), pgs. 139 et seq; and Fudenberg, et al, *Basic & Clinical Immunology*, Lange Medical Publications, Los Altos, CA. (1976), pp. 308 et seq. Also, Sawai et al, U.S. Pat. Nos. 4,118,192 and 4,208,185 relate to agglutination assays. Earlier references which are likewise relevant are Singer et al, J. Colloid and Interface Science, 45:608–614 (1973) and Faure et al, *Protides of the Biological Fluids*, Proceedings of the Colloquium, 20:589–593 (1972). A number of agglutination assay test kits for specific analytes or ligands are commercially available and have also been described in the literature. See, for example, Rose, et al (Eds.), *Manual of Clinical Immunology*, American Society for Microbiology, Washington, D.C. (1978).

When assaying complex liquids, such as human serum, some proteins and other substances can cause non-specific interferences with the agglutination reaction. Therefore, these proteins must be destroyed or their non-specific interaction with the reagents overcome to obtain accurate measurement of ligand concentrations. The most common approach to avoiding non-specific protein interference has been by first digesting the proteins with a proteolytic enzyme such as pepsin. The enzyme is then inactivated or destroyed prior to the assay. For example, Collet-Cassart, et al *Clin. Chem.*, 27:1205–09 (1981) disclose a particle-counting immunoassay for digoxin in samples which were predigested with pepsin. The digestion was stopped by adding tris (hydroxymethyl) methylamine which inactivates the pepsin. See also Chau et al, J. Clin. Endocrinol. Metab., 42:189–192 (1976).

Alternatively, these assays can be performed using particles which are not susceptible to interaction with substances that cause non-specific interference. For example, Hosaka, et al, EPO Application No. 54,249 discloses immunoassay reagents formed of an immunochemical containing an amino group, e.g. an antibody, which is covalently bound to an epoxy group on the surface of particles comprising a polymer having the repeating unit of glycidyl acrylate and/or glycidyl methacrylate. The particles are not to have other hydrophobic components on their surface. When the epoxy groups are not all consumed by binding with the above immunochemicals, hydrophilic proteins, e.g. albumin, which do not interfere with the immunoassay can be reacted with the remaining epoxy groups. It is said that these particles are unlikely to agglutinate non-specifically and are free from non-specific adhesion to cells.

SUMMARY OF THE INVENTION

In accordance with the present invention, specific binding assays are provided in which the effects of non-specific interference are avoided or overcome by a new class of solid phase, e.g., particulate, reagents. As such, these reagents make it possible to provide a homogeneous immunoassay format, i.e., requires no separation step, in which this interference has been overcome and which is particularly suitable for use in automated analysis systems.

These advantages are achieved by a hydrophilic specific binding assay reagent which reagent is prepared by a process comprising the steps of reacting a partner of a specific binding pair and at least one hydrophilic substance with haloalkyl moieties associated with the surface of a solid phase and recovering the reagent so prepared from any unreacted binding partner. Preferably, the alpha-haloalkyl is chloromethyl and the at least one hydrophilic substance comprises at least one protein, such as albumin, and at least one non-proteinaceous amine to which the solid phase is impermeable, such as tris (hydroxymethyl) aminomethane.

The specific binding assay reagent of the invention can be combined with other reagents to provide an assay composition. For example, the composition can comprise the above reagent and the other partner of said specific binding pair. The other partner of the specific binding pair is preferably a ligand-carrier complex. Various embodiments, which include or use the composition are also contemplated. For example, the composition can be provided as part of a test kit comprising the packaged combination of one or more containers of or devices incorporated with the components of the composition.

DESCRIPTION OF THE PREFERRED EMBODIMENTS

Sample fluids on which tests are performed include biological, physiological, industrial, environmental, and other types of liquids. Of particular interest are biological fluids such as serum, plasma, urine, cerebrospinal fluid, saliva, milk, broth and other culture media and supernatants as well as fractions of any of them. Physiological fluids of interest include infusion solutions, buffers, preservative or antimicrobial solutions and the like. Industrial liquids include fermentation media and other processing liquids used, for example, in the manufacture of pharmaceuticals, dairy products and malt beverages. Other sources of sample fluid which are tested by conventional methods are contemplated as within the meaning of this term as used and can, likewise, be assayed in accordance with the invention.

The term "ligand" refers to any substance, or class of related substances, whose presence is to be qualitatively or quantitatively determined in a sample fluid, such as those just described. The present assay can be applied to the detection of ligands for which there is a specific binding partner and, conversely, to the detection of the capacity of a liquid medium to bind a ligand (usually due to the presence of a binding partner for the ligand in the sample). The ligand usually is a peptide, protein, carbohydrate, glycoprotein, steroid, or other organic molecule for which a specific binding partner exists or can be provided by immunological or synthetic means. The ligand, in functional terms, is usually selected from antigens and antibodies thereto; haptens and antibodies thereto; and hormones, vitamins, metabolites and pharmacological agents and their receptors and binding substances. Specific examples of ligands which can be detected using the present invention are hormones such as insulin, chorionic gonadotropin, thyroxine, triiodothyronine, follicle-stimulating hormone, leutinizing hormone, thyroid-stimulating hormone, and estriol; antigens and haptens such as ferritin, bradykinin, prostaglandins, and tumor specific antigens; vitamins such as biotin, vitamin $B_{12}$, folic acid, vitamin E, vitamin A, and ascorbic acid; metabolites such as 3', 5'-adenosine monophosphate and 3', 5'-guanosine monophosphate; pharmacological agents or drugs such as aminoglycoside antibiotics like gentamicin, amikacin and sisomicin, or drugs of abuse such as the opium alkaloids and ergot derivatives; antibodies such as microsomal antibody and antibodies to hepatitis and allergens; and specific binding receptors such as thyroxine binding globulin, avidin, intrinsic factor, and transcobalamin.

The terms "specific binding protein" or "receptor" refer to any substance, or class of substances, which has a specific binding affinity for the ligand to the exclusion of other substances. In the majority of embodiments, the present invention will incorporate specific binding assay reagents which interact with the sample ligand or the binding capacity of the sample for the ligand in an immunochemical manner. That is, there will be an antigen-antibody or hapten-antibody relationship between reagents and/or the sample ligand or the binding capacity of the sample for the ligand. Such assays therefore are termed immunoassays and the special interaction between the ligand and its receptor, or binding partner, is an immunochemical binding. The use of either polyclonal or monoclonal antibodies is contemplated. Additionally, it is well understood in the art that other binding interactions between the ligand and the binding partner serve as the basis of specific binding assays, including the binding interactions between hormones, vitamins, metabolites, and pharmacological agents, and their respective receptors and binding substances. For example, polypeptide hormone receptors as binding agents or partners are discussed in Langan, et al, (Eds.) *Ligand Assay*, Masson Publishing U.S.A. Inc., New York, pages 211 et seq. (1981).

The "solid phase" of the present invention can take on a multitude of forms, and is therefore intended as being broad in context. It can be mono- or multi-phasic, comprising one or more appropriate materials or media of similar or different absorptive or other physical characteristics. In one embodiment the solid phase is a matrix or surface associated in any of a variety of ways with specific binding assay reagents. It can take on many known forms such as those utilized for chemical and enzymatic solution analysis. For example, the element can be in the form of a test slide, made in part from a material such as unsubstituted polystyrene. In its most efficient embodiment the solid phase can be carefully tailored to suit the characteristics of the particular specific binding assay system to be employed.

The most preferred solid phase format is particulate. As previously noted, particle-associated agglutination assays include assays using particles having specific binding pair members as surface components or particles to which such components have been bound. These particles can be formed of one or more layers and can include a core particle. The material of which the core or layers, other than the surface layer, is formed are not critical. Whether of multilayer or uniform composition, they can be of insoluble polymers or copolymers prepared from such monomers as styrene, substituted styrenes, butadiene, acrylic acid, acrylic esters, acrylamide, acrylonitrile, the corresponding methacryloyl monomers (including functional esters, e.g., glycidyl ester), and bifunctional monomers (crosslinkers) such as divinyl benzene, methylene N,N'-bisacrylamide and many others. These particles preferably range in size from about 0.05 to about 5.0 microns in diameter and form a latex, e.g., a free-flowing liquid in which such microscopic particles are suspended.

The solid phase, such as a particle, is selected or synthesized to have on its surface a haloalkyl moiety in which the halogen is activated by virtue of its relative position to groups to which it is attached. To those skilled in the art it is known that electron donating groups, such as aryl, carbonyl, nitrile, sulphone and sulphoxide, render halogens in the alpha position quite reactive. In context with this invention, the term haloalkyl comprises the bromide and chloride substituted lower alkyl chains, e.g., C1 to C4. These groups are attached to the polymer surface in such manner that the halogen is in the alpha position to an activating group, e.g., phenyl group. Particles of this sort and their preparation are described, for example, in Vituske, et al, U.S. Pat. No. 3,072,588.

A binding partner, such as an antibody, is bound to the solid phase by replacement of the halide group on the alphacarbon of the alkyl moiety. Since this binding partner is usually a protein, whether antibody or other protein, there are numerous amino and sulfhydryl groups which can effect this substitution thereby covalently coupling the binding partner to the solid phase. The proportions of alpha-haloalkyl moieties on the solid phase and the binding partner are such that the moieties are not all coupled with binding partner.

At least one hydrophilic substance is reacted with others of the alpha-haloalkyl moieties, either sequentially or concurrently with the binding partner. When this hydrophilic substance is bound to the solid phase sequentially, it can be done either before or after binding of the binding partner. In either case, the hydrophilic substance binds a sufficient number of remaining moieties to create, with the binding partner, a substantially complete hydrophilic coating on the surface of the solid phase.

Preferably, the hydrophilic substance includes at least one protein and at least one non-proteinaceous amine to which the solid phase is substantially impermeable. Examples of preferred proteins are human and other serum albumins or gelatin. For this purpose, peptides are also contemplated when the term protein is used. Examples of non-proteinaceous amines are tris (hydroxymethyl) aminomethane, diethanolamine, triethanolamine, glucosamine, glycine, lysine, glutamate, e-aminocaproic acid or polyglycolamines.

The above-described specific binding assay reagent can be combined with other reagents to provide an assay composition. Usually the other reagents include the other partner of the specific binding pair and is kept physically separate from the solid phase reagent of the invention until used in performing an assay. Preferably the partner of the specific binding pair which is associated with the solid phase is an antibody and the other partner of the pair is a ligand which has been bound to a carrier to form a ligand-carrier-complex. Exemplary of such carriers are high molecules weight polymers such as dextran or Ficoll (Pharmacia Fine Chemical, Inc., New Market, N.J.). Among the other reagents which can be included are proteolytic enzymes such as trypsin, chymotrypsin, pepsin, carboxypeptidase and mixtures thereof.

The composition can be provided in the form of a kit comprising the packaged combination of one or more containers of or devices incorporated with the components of the composition. For example, the solid phase reagent of the invention can be coated on or form part of a test slide, preferably having an indented reaction well. Binding partner from a separate container of the kit and a sample to be analyzed are placed in the reaction well and any resultant change, such as agglutination or a color change, is visually observed. Such kits are ideal for home use and require no prior technical training.

The following working example describes experiments which were performed in developing the present invention. Standard commercially available reagent grade chemicals were used whenever possible.

EXAMPLE I

Measurement of total serum thyroxine ($T_4$) is the single most important test for determining thyroid function. The normal $T_4$ range is 4.5 to 12.0 micrograms/deciliter (ug/dl); however, the test must be able to detect concentrations as low as 1.0 ug/dl and as high as 24.0 ug/dl. This is necessary to accurately identify those patients who have thyroid disorders. This Example reports experiments which demonstrate a nonisotopic, homogeneous $T_4$ immunoassay in accordance with the invention.

ANTISERA PREPARTION

Antibody to $T_4$ was induced in New Zealand white rabbits by an intradermal primary injection of 400 ug of a conjugate which was $T_4$ covalently coupled to bovine serum albumin (BSA) emulsified in an equal volume of Freund's complete adjuvant. Secondary booster immunizations contained 400 ug of $T_4$-BSA conjugate emulsified in an equal volume of incomplete Freund's adjuvant and were administered once a month. The animals were bled three times a week.

ANTIBODY PURIFICATION

The antibody so prepared was isolated by immunoadsorbtion. The immunoadsorbent consisted of $T_4$ covalently bound to Sepharose 4B (Pharmacia Fine Chemicals, Iscataway, N.J.). This material was prepared using the bisoxirane method described by Sundberg and Porath in J. Chromatog., 90:87–98 (1974). Five milliliters (ml) of the immunadsorbent were packed on top of 25 ml of Sephadex G-25 (Pharmacia, supra) in a 2×20 centimeter (cm) glass chromatography column. Five ml of antiserum, prepared as described above, were applied to the column and allowed to enter the column until the red or amber color reached the immunoadsorbent-Sephadex interface. The antiserum was allowed to remain in contact with the adsorbent for an additional 30 minutes at room temperature. The immunoadsorbent was then washed with two column volumes of barbital buffered saline (0.05 M barbital, 0.15 M NaCl, 0.1% $NaN_3$, pH 8.6) followed by a quantity of borate buffered saline (0.04 M borate, 0.15 M NaCl, 0.1% $NaN_3$, pH 8.1) sufficient to bring the absorbence of the effluent at 280 nanometers (nm) to less than 0.01. At this point the adsorbed antibody was eluted with 1.0 M acetic acid. The eluant was collected in 1 ml aliquots with a fraction collector. Those fractions with an absorbence at 280 nm greater than 0.1 and a pH greater than 7.0 were pooled and stored at $-20°$ centigrade (C.) until used. Typically 1–2 milligrams (mg) of purified antibody were isolated from 1 ml of antisera.

ANTIBODY SENSITIZED LATEX PREPARATION

This reagent preparation makes use of a poly (chloromethyl styrene) latex which was prepared substantially as described in Vitkuske, et al, U.S. Pat. No. 3,072,588. The antibody to $T_4$, human serum albumin and tris (hydroxymethyl) aminomethane are coupled to the poly (chloromethyl styrene) particles as follows. A 1 ml volume of 10% (w/v) poly (chloromethyl styrene) particles in water is mixed with 1 ml of a 0.2 mg/ml sodium dodecyl sulfate aqueous solution to form a latex suspension. This suspension was then centrifuged at 30,000×g for 20 minutes, forming a pellet of the particles from the suspension. This pellet is resuspended to visual homogeneity by sonication in 2 ml of borate buffered saline (pH 9.0) containing 0.01 mg/ml sodium dodecyl sulfate. A 2 ml volume of this resuspension is combined with 2 ml of an aqueous solution containing 700 micrograms (ug) of the anti $T_4$-antisera and 15 mg of charcoal-treated human serum albumin. The 4 ml suspension so prepared was then incubated for 4 hours at 30° C. After incubation, this suspension was then centrifuged at 30,000×g for 20 minutes, forming a pellet of the antibody and albumin coated particles from the suspension. This pellet of coated particles was then resuspended by sonication in 5 ml of 1 molar (M) tris (hydroxymethyl) aminomethane (pH 10). This binds with chloromethyl moieties which had not previously been bound, with antibody or albumin, to complete the hydrophilic surface. The suspension was incubated for 16 hours at 30° C.

Then, the suspension was centrifuged at 30,000×g for 20 minutes to form a pellet. The pellet was resuspended in 6 ml of carbonate buffered saline containing 0.1% (w/v) of charcoal stripped bovine serum albumin and 0.1% (w/v) Tween 20 surfactant (ICI United States, Inc., Wilmington, Del.). The pellet was centrifuged and resuspended in carbonate buffer, as just described, six more times to further free it of unbound antibody. The suspension so prepared was used as described below.

T$_4$-DEXTRAN CONJUGATE PREPARATION

T$_4$ was covalently coupled to cyanogen bromide activated Dextran T500 (Pharmacia, supra). One hundred milligrams (mg) of Dextran was dissolbed in 6 ml of 0.4 M K$_2$CO$_3$ and the pH was adjusted to 11.0. The solution was rapidly stirred and three, fifty ul additions of cyanogen bromide solution (333 mg/ml in N,N-dimethyl-formamide) were made. The pH of the Dextran solution was maintained at 11.0 by the addition of 2 N NaOH. Each addition of cyanogen bromide was made within one minute of the previous addition and after the last addition the solution was incubated for four minutes. The pH was then dropped to 10.0 with 2 N HCl and 0.5 ml of a T$_4$ solution was added (80 mg/ml in N,N-dimethyl-formamide made alkaline with 11–15 drops of 0.4 M K$_2$CO$_3$). The reaction mixture was stirred for two hours at room temperature then dialyzed exhaustively against 0.01 M Na$_2$HPO$_4$ (pH 9.0). Typically, 60–70 moles of T$_4$ were incorporated into each mole of Dextran. The T$_4$ Dextran conjugate concentration was 10 mg/ml. This was diluted in a buffer solution containing 0.05 M barbital, 0.15 M NaCl, and 0.1% azide, pH 8.6 (Veronal buffer) to 10 ug/ml just prior to use in the assay procedure described below.

ANTIBODY SENSITIZED LATEX REAGENT PREPARATION

A 5 ml volume of the antibody sensitized latex reagent preparation was prepared as follows. A 1.66 ml volume of the antibody sensitized latex stock solution, prepared as described above, was mixed with 533 ul of a solution containing 0.55 mg/ml 8-anilino-1-naphthalenesulfonic acid (ANS) (Eastman Kodak Co., Rochester, N.Y.) in Veronal buffer containing T$_4$-free 0.1% bovine serum albumin (Veronal/BSA), 2.08 ml of a solution containing 20 mg/ml trypsin in 1 mM aqueous HCl, 62.5 ul of Tween 20 surfactant (ICI United States, Wilmington, DE) that was 10% (v/v) in Veronal/BSA and 654 ul of Veronal/BSA. The final concentrations were 0.11% (w/v) of latex solids, 0.059 mg/ml (ANS) and 8.3 mg/ml trypsin.

ASSAY PROCEDURE AND RESULTS

A panel of six (6) serum samples were tested for T$_4$ level by an assay method using particles in accordance with the invention, the same assay method using conventional latex reagent particles, carboxylated polystyrene (Rhone-Poulenc, Paris, France), and by a reference method. The agglutination method using the disclosed and conventional particles was also performed on a range of T$_4$ standard sera (Kallestad Laboratories, Inc., Austin, Tex.).

For the methods using the particles of the invention and the conventional particles, a 12.8 ul aliquot of each serum standard or serum sample was introduced into a separate tube (packed in ice) containing 12.8 ul T$_4$-Dextran conjugate, as diluted. Thereafter, 120 ul of the antibody sensitized latex reagent was introduced into each of the tubes. Each of the tubes containing the complete reaction mixture so formed was vortexed and then incubated at 37° C. for 15 minutes. Incubation was terminated by ice water immersion. Each reaction mixture was diluted by addition of 0.8 ml Veronal buffer and the diluted mixture was introduced into a 1.0 cm quartz cuvette. In each case, the cuvette was then placed in a Beckman DBG spectrophotometer (Beckman Instruments, Inc., Fullerton, Calif.) and the absorbance at 600 nm wavelength was read. The absorbance values were mathematically converted to T$_4$ concentration values.

The reference method was the Gammaflo assay (E. R. Squibb & Sons, Inc., Princeton, N.J.) method which was performed according to the manufacturers directions.

The T$_4$ concentrations observed for these serum samples by the reference method and the methods using conventional particles and the chloromethyl-substituted particles of the invention are set forth in Table 1.

TABLE 1

| REFERENCE GAMMAFLOW METHOD | CONVENTIONAL LATEX METHOD | DISCLOSED LATEX METHOD |
|---|---|---|
| 5.6 (μg/dl) | 4.7 | 7.5 |
| 6.8 | 3.9 | 7.7 |
| 7.6 | 8.2 | 7.7 |
| 8.0 | >25.1 | 5.7 |
| 9.5 | 6.9 | 8.8 |
| 10.6 | >25.1 | 10.6 |

As can be seen from these data, the conventional latex method was subject to interference in two of the six samples tested. The interference caused clearly erroneous reported concentrations which were well above the concentrations found by the reference and disclosed methods. The erroneous values were well above the highest commercial standard sera run (25.1 ug/dl), which rendered these results useless. In contrast, the T$_4$ concentrations observed using particles in accordance with the invention correlated well with the values given by the reference method. This demonstrates that the non-specific interference which plagued the conventional method has been avoided or overcome by this invention.

What is claimed is:

1. A hydrophilic specific binding assay reagent which is prepared by a process comprising the steps of reacting a partner of a specific binding pair and at least one hydrophilic moiety with haloalkyl moieties present on the surface of a solid phase thereby covalently coupling said partner of a specific binding pair and said at least one hydrophilic moiety to said solid phase to create a substantially complete hydrophilic coating thereon, said at least one hydrophilic moiety including at least one protein and at least one non-proteinaceous amine to which said solid phase is substantially impermeable and recovering the reagent so prepared from any unreacted binding partner.

2. The specific binding assay reagent of claim 1 wherein the haloalkyl is chloroalkyl.

3. The specific binding assay reagent of claim 1 wherein said solid phase is particulate.

4. The specific binding assay reagent of claim 3 wherein said particulate solid phase is polymeric.

5. The specific binding assay reagent of claim 1 wherein said solid phase comprises a haloalkyl substituted polystyrene.

6. The specific binding assay reagent of claim 1 wherein said specific binding pair partner is an antibody.

7. The specific binding assay reagent of claim 6 wherein said antibody is a polyclonal or monoclonal antibody.

8. The specific binding assay reagent of claim 1 wherein said at least one non-proteinaceous amine is tris (hydroxymethyl) aminomethane.

9. The specific binding assay reagent of claim 1 wherein said at least one protein is albumin.

10. A process of preparing a specific binding assay reagent which comprises the steps of reacting a partner of a specific binding pair and at least one hydrophilic moiety with haloalkyl moieties present on the surface of a solid phase, thereby covalently coupling said partner of specific binding pair and said at least one hydrophilic moiety to said solid phase to create a substantially complete hydrophilic coating thereon, said hydrophilic moiety including at leaast one protein and at least one non-proteinaceous amine to which said solid phase is substantially impermeable, and recovering the reagent so-prepared from any unreacted binding partner.

11. A specific binding assay test composition for determining a ligand in a liquid sample which comprises: (a) a hydrophilic specific binding assay reagent which is prepared by a process comprising the steps of reacting a partner of a specific binding pair and at least one hydrophilic moiety with haloalkyl moieties present on the surface of a solid phase, thereby covalently coupling said partner of a specific binding pair and said at least one hydrophilic moiety to said solid phase to create a substantially complete hydrophilic coating thereon, said hydrophilic moiety including at least one protein and at least one non-proteinaceous amine to which said solid phase is substantially impermeable, and recovering the reagent so-prepared from any unreacted binding partner; and (b) the other partner of said specific binding pair.

12. The specific binding assay test composition of claim 11 wherein the haloalkyl is chloromethyl.

13. The specific binding assay test composition of claim 11 wherein said at least one protein is albumin.

14. The specific binding assay test composition of claim 13 wherein said at least one non-proteinaceous amine is tris (hydroxymethyl) aminomethane.

15. The specific binding assay test composition of claim 11 wherein the specific binding pair partner bound to the solid phase is an antibody and the other partner of the specific binding pair is a ligand or specific binding analog thereof.

16. The specific binding assay test composition of claim 11 wherein said solid phase is particulate.

17. The specific binding assay test composition of claim 16 wherein said specific binding assay reagent is a latex.

18. The specific binding assay test composition of claim 17 wherein said the specific binding assay reagent comprises an antibody associated with particles in said latex.

19. The specific binding assay test composition of claim 18 wherein said antibody is a polyclonal or monoclonal antibody.

20. A specific binding assay method for determining a ligand in a liquid sample, which method comprises combining said sample in a reaction mixture with the composition of any of claims 12, 11 or 15 and detecting any resultant binding of the partners of the specific binding pair.

* * * * *